United States Patent [19]

Ferguson

[11] 4,254,580
[45] Mar. 10, 1981

[54] PRODUCTION OF SUNFLOWER SEEDS IN INCREASED YIELDS

[75] Inventor: David B. Ferguson, Fresno, Calif.

[73] Assignee: David & Sons, Inc., Fresno, Calif.

[21] Appl. No.: 953,786

[22] Filed: Oct. 23, 1978

[51] Int. Cl.³ .............................................. A01H 1/02
[52] U.S. Cl. .................................... 47/58; 47/DIG. 1
[58] Field of Search .......................... 47/1, 58, DIG. 1

[56] References Cited

U.S. PATENT DOCUMENTS

| | | | |
|---|---|---|---|
| 3,570,181 | 3/1971 | Davis | 47/58 |
| 3,903,645 | 9/1975 | Bradner | 47/58 |

*Primary Examiner*—Robert E. Bagwill
*Attorney, Agent, or Firm*—Burns, Doane, Swecker & Mathis

[57] ABSTRACT

The production of sunflower seeds (i.e. *Helianthus annus* seeds) is an important industry in the United States as well as in many other parts of the world. Such seeds are useful in the production of sunflower oil or may serve as a food source for man and other animals. The present invention provides a novel and highly effective technique for enhancing the production of sunflower seeds via an agricultural process wherein a greater proportion of the florets which make up the sunflower are effectively pollinated. The production of sunflower achene which lack the desired kernels accordingly is minimized and a greater seed yield is made possible per growing area. Such process utilizes as an essential element a substantially uniform population of sunflower seed parents (as described) which were developed by applicant and possess homozygous f genes having the ability to facilitate the formation of parenchyma cells between floret anthers (instead of the typical collenchyma cells) which enable the anthers to become substantially non-fused following pollen dehiscense thereby making possible a greater degree of self-pollination with concomitant increased seed formation. In a further preferred embodiment $F_1$ hybrid sunflower seeds are produced (as described). Alternatively, sunflower seeds capable of perpetuating inbred sunflower lines efficiently may be produced in increased yields on a commercially practicable basis.

17 Claims, 13 Drawing Figures

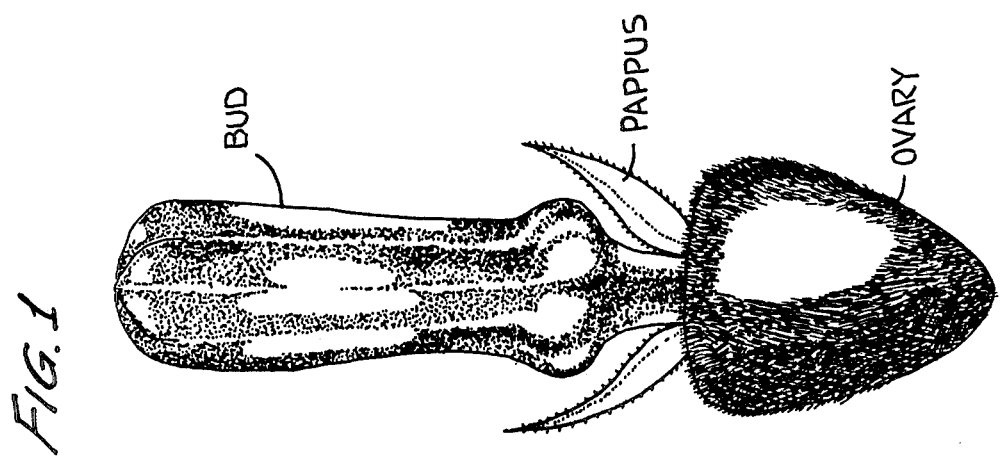
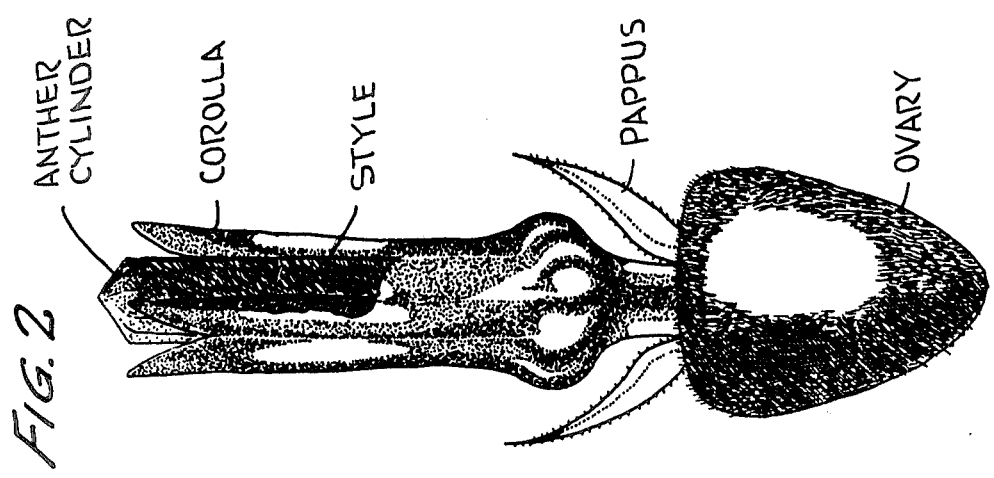
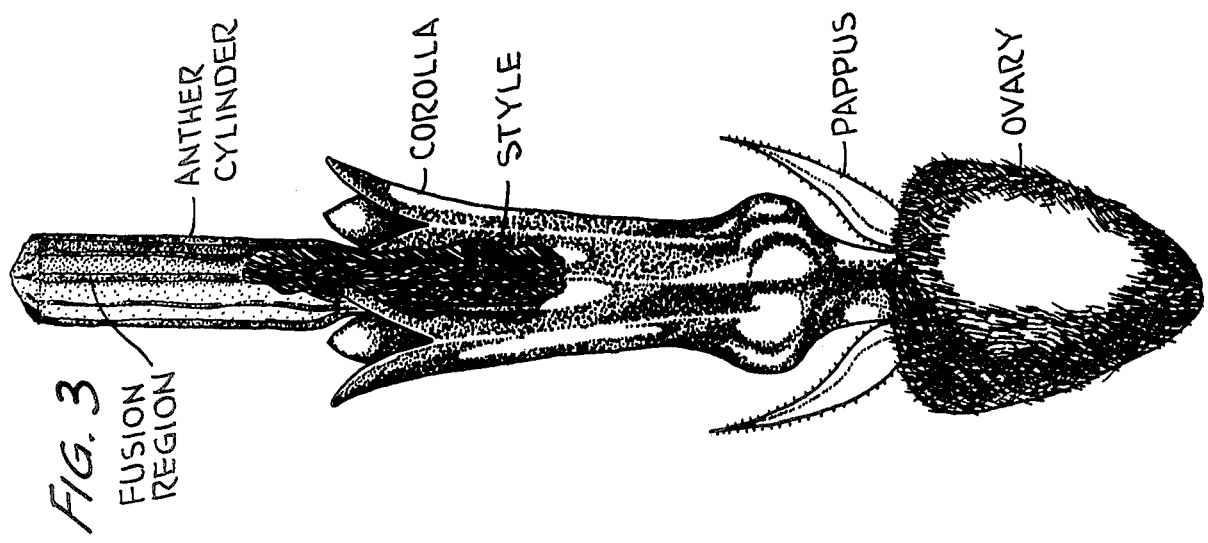

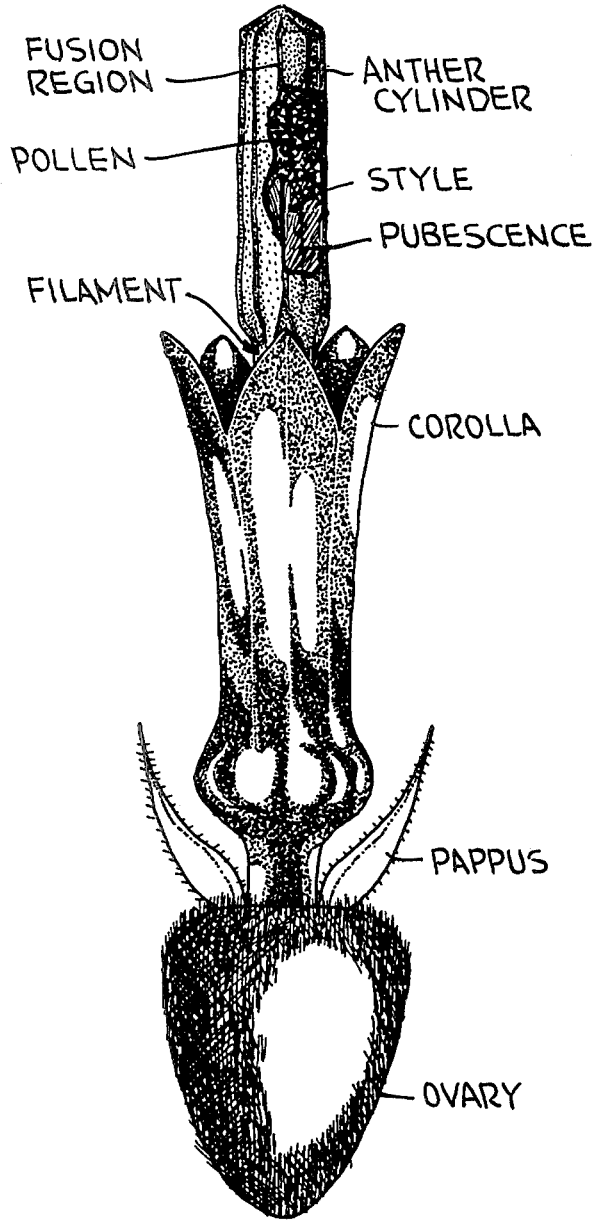
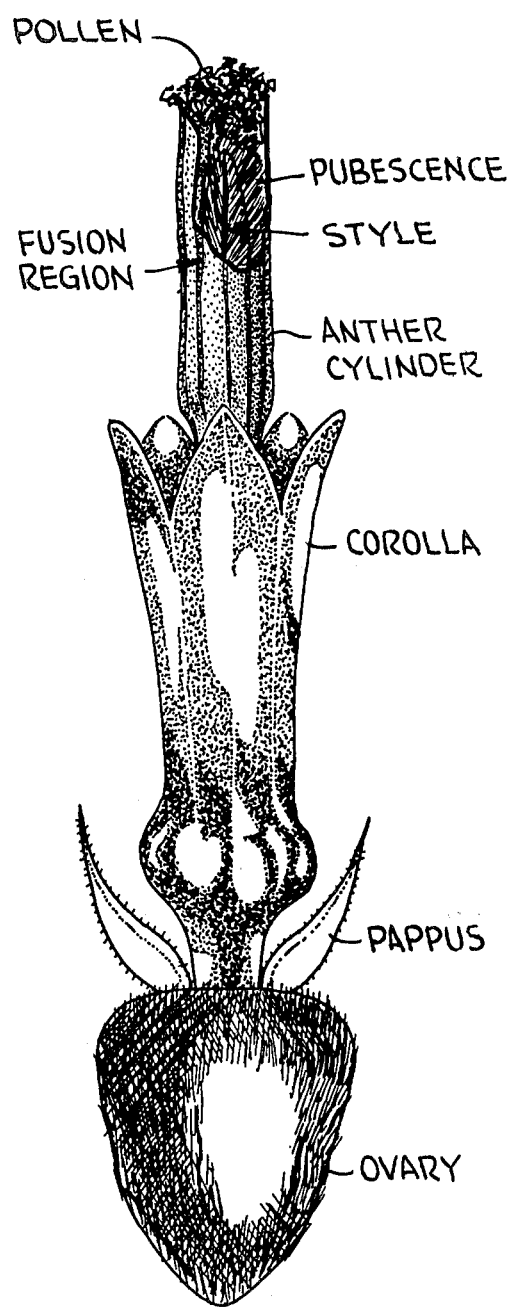

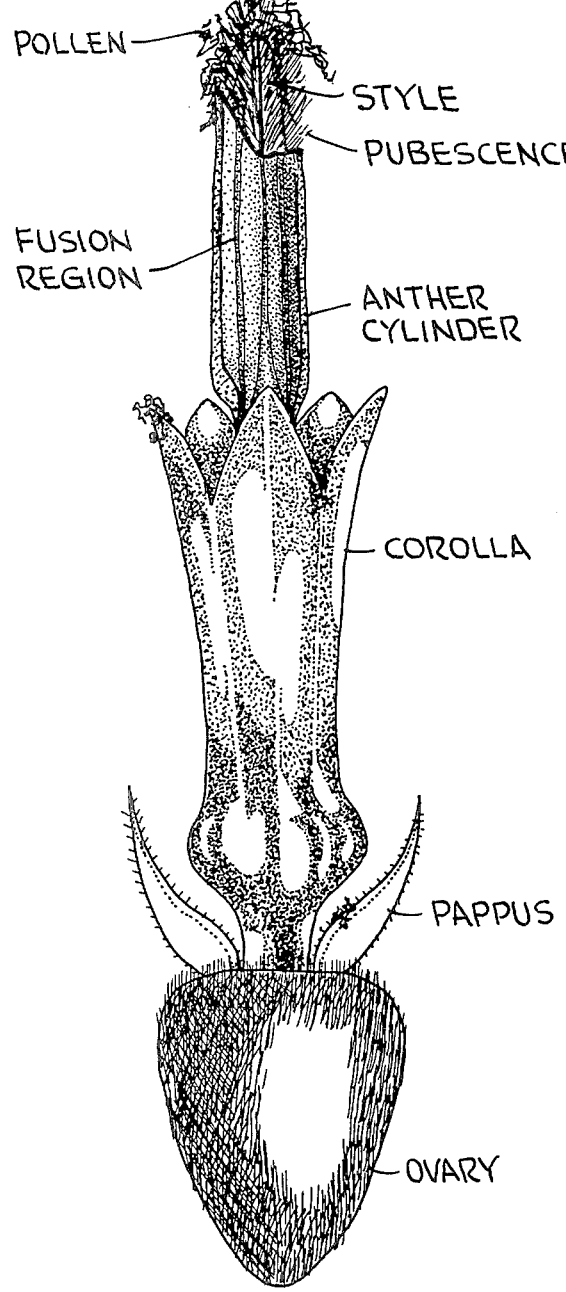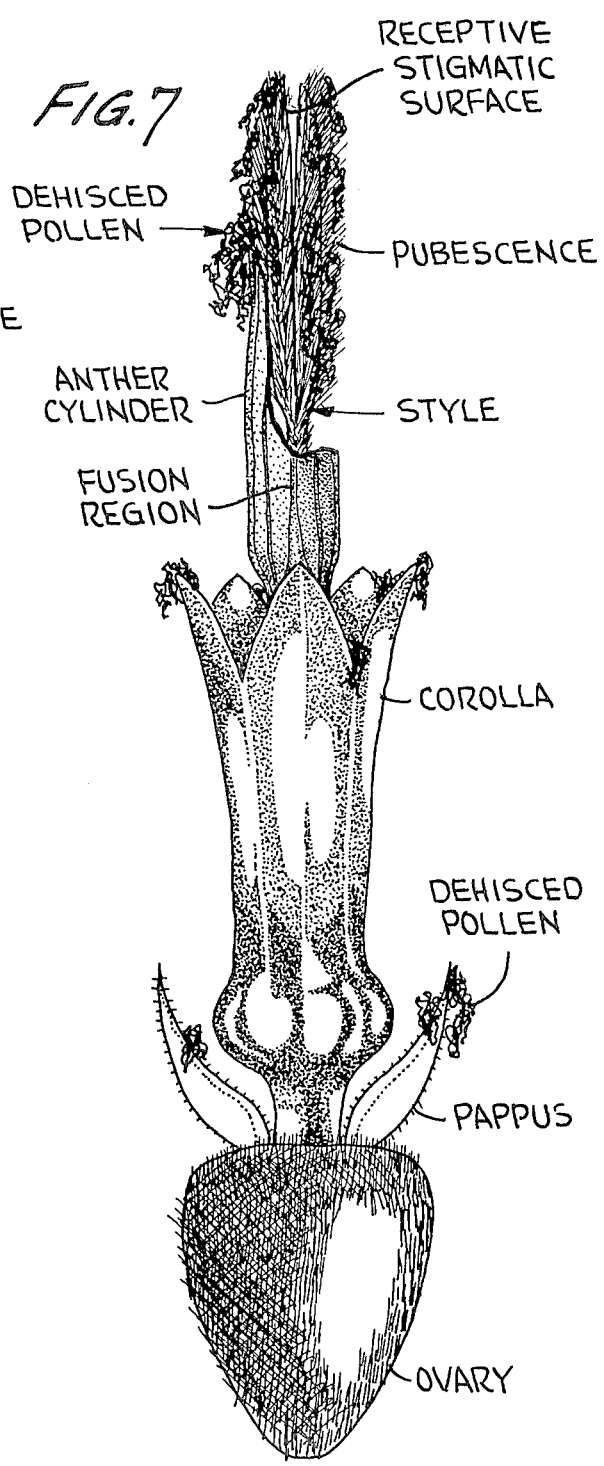

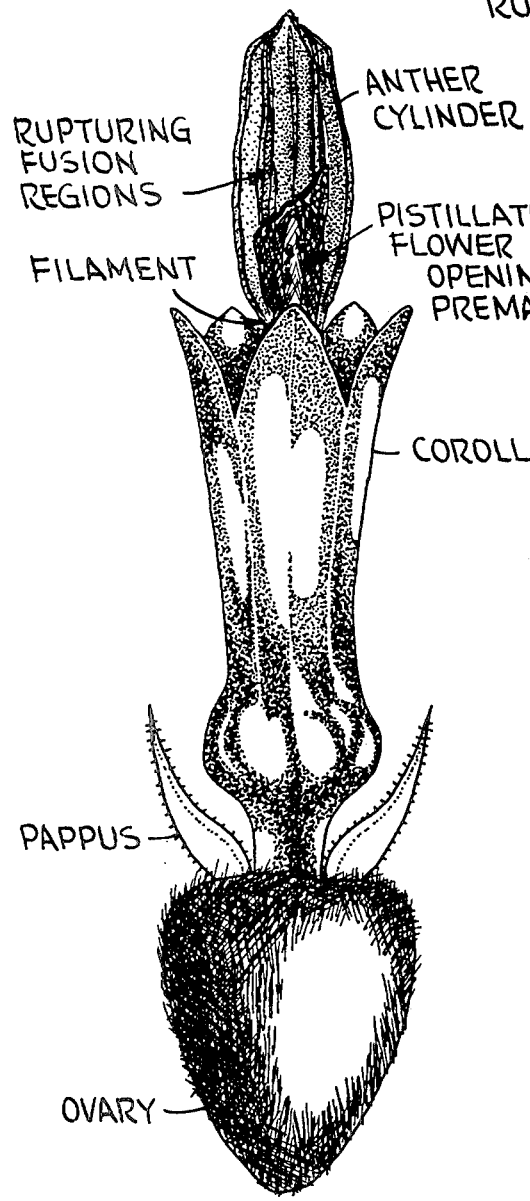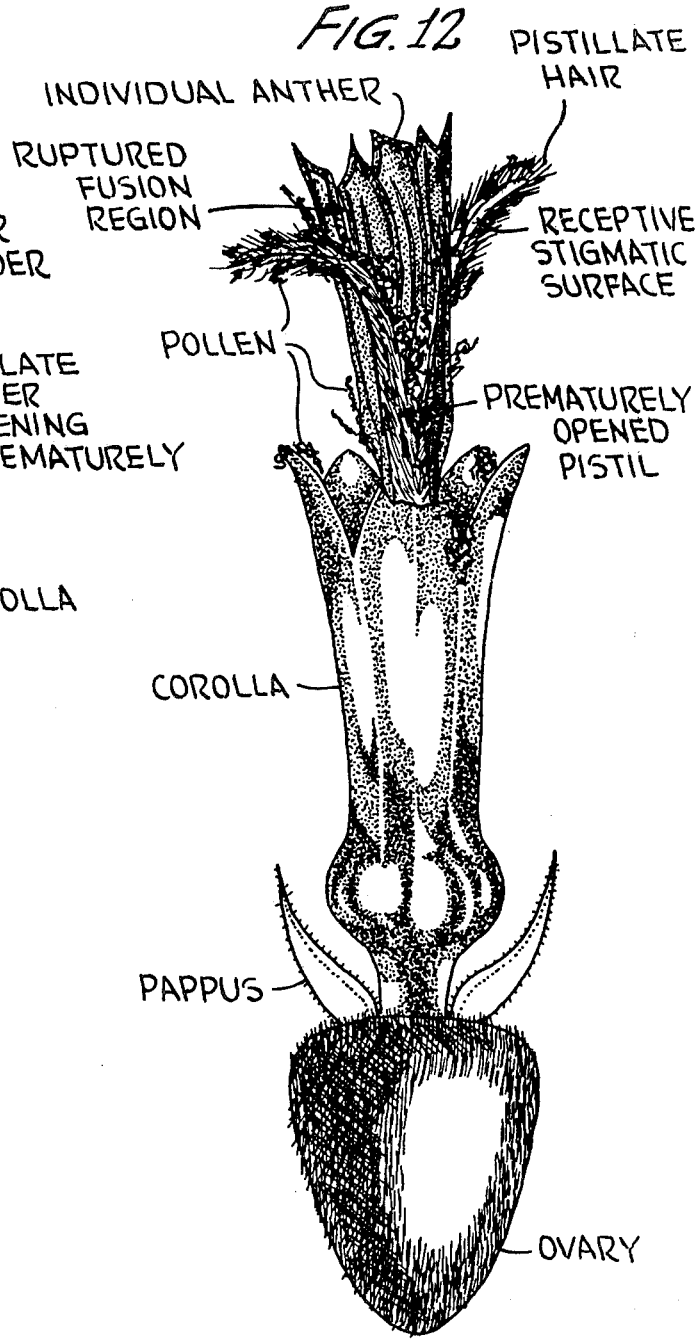

PRODUCTION OF SUNFLOWER SEEDS IN INCREASED YIELDS

BACKGROUND OF THE INVENTION

The formation and harvesting of sunflower seeds (i.e. *Helianthus annuus* seeds) is recognized to be an important industry of considerable economic impact in various sectors of the world. For instance, it is estimated that annually in excess of two million acres presently are commercially being planted in sunflower plants throughout the United States of America. Additionally, existing trends point to the increased growing of sunflowers as a source of both oil and food. See, "The Sunflower" by Charles B. Heiser, Jr., published by the University of Oklahoma Press (1976)

The sunflower plant has not escaped study by plant scientists over the years. It possesses perfect flowers which possess both male and female elements and in theory can undergo either self-fertilization or cross-fertilization. It further is well recognized that the sunflower blossom is composed of many individual florets (e.g. 500 to 1,000 florets arranged side by side as a disk) which must be individually pollinated if each is to result in the formation of a sunflower achene which includes a kernel. Since the kernel serves as the source of food for men and livestock, as well as the source of sunflower oil, such pollination is essential and of prime importance.

Naturally occurring sunflower plants found in nature are recognized to possess a high degree of physiological or sporophytic self-incompatibility (i.e. they are self-unfruitful) and accordingly commonly undergo at most only a slight degree of self-fertilization. The bulk of the fertilization which occurs in such sunflower plants must accordingly be the result of pollen derived from other sunflower plants growing in the same general area which is primarily transferred by insect vectors. See Page Nos. 18 and 19 of the Heiser treatise. Since normally occurring insect populations are commonly incapable of servicing literally billions of individual florets in a growing area where such sunflower plants are growing in large numbers, the resulting seed set commonly is poor among large concentrations of sunflower plants growing in nature.

It additionally is recognized that the longevity of sunflower pollen is influenced by the environment it encounters following dehiscence. For instance, if the days are hot (e.g. 100° F.) and the relative humidity low (e.g. 20 percent or less) the pollen may live for only a few hours at most once it is exposed to the environment. However, when the temperature is lower (e.g. 70° to 75° F.) and the relative humidity is higher (e.g. 40 to 45 percent), the sunflower pollen may live for several days (e.g. up to three days). There accordingly is recognized to be a finite period of time in which sunflower pollen can satisfactorily carry out its intended function.

Over the years the research of sunflower breeders has resulted in the development of sunflower cultivars which are agronomically improved over those sunflowers commonly found growing in nature. For instance, some cultivars commonly are capable of undergoing a greater degree of self-pollination assuming advantageous growing conditions are encountered. At least some of the physiological self-incompatibility is overcome in such cultivars and it is possible for the stigma to curve around and to eventually contact its own pollen and accomplish fertilization assuming it has not already been killed due to adverse environmental conditions. However, even under the most advantageous environmental conditions such self-fertilization is still limited and falls far short of accomplishing pollination of all the individual florets encountered in a commercial growing area where such plants are grown.

Other researchers have taken a different approach and have attempted to develop a technique for producing seeds capable of forming $F_1$ hybrid sunflower plants which relies largely upon the use of self-incompatible sunflower plants as seed parents so that self-pollination is impossible. Such technique, however, required the substantial utilization of insect vectors, and posed an insurmountable problem for the $F_1$ hybrid sunflower seed producer when he attempted to maintain the largely self-incompatible seed parent line on a commercially practicable basis. Such approach has not been a commercial reality.

In more recent years cytoplasmic male sterile sunflower plants have been discovered as well as maintainer sunflower plants for the same which has made possible the production of other synthetic $F_1$ hybrid sunflower cultivars which presently are being commercially marketed for use by sunflower growers in the United States. Such cultivars constitute a significant advance in the production of sunflower plants since they offer the grower the prospect of obtaining hybrid vigor in his crop. There, nevertheless, still have remained significant shortcomings in this approach. For instance, pollen transfer by insect vectors still is essential both in the production of the hybrid sunflower seed and when grown by the farmer if adequate seed formation is to be achieved. The sunflower grower commonly will not have available the required insect population to accomplish efficient pollen transfer. He accordingly is at the mercy of the local insect population and the weather which influences the longevity of the pollen awaiting transfer by the insects. A high degree of pollen transfer is largely impossible unless high concentrations of insect vectors can saturate the area, and the weather conditions are such that the life of the pollen from the pollinator is not unduly attentuated. Factors having a significant economic impact are to a large extent outside the control of the grower.

Others have proposed that the development of sunflower cultivars having shorter anthers might possibly make it easier for bees or other insects to forage for pollen and nectar within the sunflower blossom and thereby aid in raising the level of cross-pollination. Such an approach has not been a commercial reality.

Additionally, commercial sunflower growers commonly have had to cope with another problem in the form of the sunflower head moth (i.e. *Homeosoma ellectelum*) which deleteriously influences the sunflower seed harvest. Such insects if unchecked can destroy the sunflower blossom and the desired crop of sunflower seeds. Accordingly, it has been necessary to treat the sunflower blossoms with an insecticide to control this harmful insect. However, the timely application of an insecticide to limit the damage done by this insect pest also results in the destruction of other desirable insect vectors (e.g. honey bees) which are required in great numbers if pollen is to be transferred to the sunflowers to accomplish seed set.

It is an object of the present invention to provide an improved process for the production of sunflower seeds.

It is an object of the present invention to provide a process for the production of sunflower seeds in increased yields thereby offering the sunflower grower a significant economic advantage.

It is an object of the present invention to provide a process for the production of sunflower seeds wherein the pollination of each floret of the sunflower blossom is facilitated thereby resulting in an enhanced seed formation.

It is an object of the present invention to provide an improved sunflower seed product which can be utilized by a sunflower grower to more reliably accomplish the pollination required for sunflower seed production without the necessity of relying upon pollen-carrying insect vectors.

It is an object of the present invention to provide an improved process for the production of sunflower seeds which are capable of growing $F_1$ hybrid sunflower plants.

It is an object of the present invention to provide an improved process for the production of sunflower seeds which is capable of maintaining an inbred sunflower line on a more efficient basis.

It is another object of the present invention to provide a process for the production of sunflower seeds which in at least some embodiments is not adversely influenced by the treatment of the sunflower blossoms with an insecticide.

It is a further object of the present invention to provide a process for the production of sunflower seeds in increased yields which is capable of accomplishing a satisfactory level of pollination even if following pollen dehiscence the florets are subjected to thunder showers and/or sprinkler irrigation which would normally result in pollen loss.

These and other objects, as well as the scope, nature, and utilization of the invention will be apparent from the following detailed description and appended claims.

SUMMARY OF THE INVENTION

It has been found that a process for the production of sunflower seeds in inceased yields comprises:

(a) planting in a growing area a plurality of seeds capable of forming Helianthus annuus sunflower plants which are physiologically self-compatible and possess homozygous f genes, the planting being carried out in the substantial absence of seeds capable of forming Helianthus annuus sunflower plants which are physiologically self-incompatible and/or lack homozygous f genes, whereby the seeds germinate to form sunflower plants, and seeds are formed on the sunflower plants as a result of self-pollination, the f genes having the ability to facilitate the formation of parenchyma cells between floret anthers which allow the anthers to become substantially non-fused following pollen dehiscense thereby making possible a greater degree of selfpollination with concomitant increased seed formation, and (b) harvesting the resulting seeds formed on the sunflower plants.

It has been found that a process for the production of sunflower seeds capable of forming $F_1$ hybrid sunflower plants which yield sunflower seeds in increased yields comprises:

(a) growing a first substantially uniform population of male sterile Helianthus annuus sunflower plants which possess homozygous f genes, the f genes having the ability to facilitate the formation of parenchyma cells between floret anthers which allow the anthers in the resultant hybrid to become substantially non-fused following pollen dehiscence, (b) growing a second substantially uniform population of male fertile Helianthus annuus sunflower plants which possess homozygous f genes in pollinating proximity to the first substantially uniform population, (c) cross-pollinating the plants of the first substantially uniform population with pollen derived from the plants of said second population with the aid of pollen-carrying insects, and (d) selectively recovering sunflower seeds which are formed upon the plants of the first population.

An improved Helianthus annuus seed product also is provided which consists of a substantially homogeneous assemblage of seeds which upon growth yield sunflower plants which are physiologically self-compatible and possess homozygous f genes, wherein the f genes facilitate the formation of parenchyma cells between floret anthers which allow the anthers to become substantially non-fused following pollen dehiscence thereby making possible a greater degree of self-pollination with a concomitant increased seed formation.

DESCRIPTION OF THE DRAWINGS

The sunflower plants under discussion are being grown in an environment having a warm ambient air temperature and a relatively high level of early morning solar radiation.

FIG. 1 is an enlarged schematic presentation of a typical sunflower floret at the mature unopened bud stage. This illustrates a typical sunflower floret the evening prior to bloom.

FIG. 2 is an enlarged schematic presentation of the typical sunflower floret on the next day at approximately 15 to 30 minutes prior to dawn. The end of the bud has opened and the tip of the anther cylinder is exposed. The corolla and anther cylinder surrounding the style are partially cut away so that the style is visible. The corolla with its five fused petals is open at the end.

FIG. 3 is an enlarged schematic presentation of the typical sunflower floret at dawn. The normal fused anther has been projected upward and lifted off the style by the elongation of the filaments (not shown). The corolla and the normal fused anther cylinder surrounding the style are partially cut away so that the style is visible. The corolla have opened.

FIG. 4 is an enlarged schematic presentation of the typical sunflower floret at approximately 30 minutes following dawn. The normal fused anther cylinder has been partially cut away to expose the style. The pollen has dehisced from the inner walls of the fused anther cylinder and the style has begun to elongate upwardly and to compact the pollen in the closed anther cylinder. No stigmatic surfaces are exposed to the receipt of pollen.

FIG. 5 is an enlarged schematic presentation of a typical sunflower floret at approximately 1 hour following dawn. A portion of the normal fused anther cylinder has been cut away to expose the style. The continued elongation of the style has forced open the end of the normal anther cylinder and begun to push the previously dehisced pollen out the opening at the end of the anther cylinder. Such pollen is being exposed to pollen-carrying insects before its own stigmatic surfaces are available.

FIG. 6 is an enlarged schematic presentation of a typical sunflower floret at approximately 1½ hours following dawn. A portion of the normal fused anther cylinder has been cut away to expose the style. The style has begun to push substantially all of the pollen out of the opening at the end of the normal fused anther cylinder. The hairs on the style serve to sweep the inner walls of the anther cylinder clean, and some of the pollen tends to cling to such hairs.

FIG. 7 is an enlarged schematic presentation of a typical sunflower floret approximately 2 hours following dawn. A portion of the normal fused anther cylinder has been cut away to expose the style. Most of the pollen now has been extruded out of the open end of the normal fused anther cylinder. Also, the style now has begun to separate into two branches and to beging to expose for the first time the receptive stigmatic surfaces which are created as the style branches separate. At this point the pollen has already been effectively dispersed and does not contact the receptive stigmatic surfaces.

FIG. 11 is an enlarged schematic presentation of the atypical sunflower floret at approximately 30 minutes following dawn. Sunflower plants possessing this atypical characteristic were developed by me as described herein. A portion of the anther area is cut away to expose the style. The pollen has dehisced from the inner walls of the anther cylinder, and parenchyma cells between floret anthers have ruptured and become substantially non-fused. Additionally, the pistillate flower portion is opening prematurely thereby exposing the receptive stigmatic surfaces to recently dehisced pollen. Compare FIG. 11 to the normal sunflower floret illustrated in FIG. 4 at the same period of time.

FIG. 12 is an enlarged schematic presentation of the atypical sunflower floret developed by me at 1 to 1½ hours following dawn. This illustrates the total rupturing of the fusion regions of the anther cylinder and the concomitant premature opening of the style branches. Recently dehisced pollen is resting on the exposed receptive stigmatic surfaces. No longer must one rely upon the time consuming "ram's horn" curl illustrated in FIG. 9. I accordingly have provided for the first time a mechanism whereby the major mechanical impediment to self-fertilization in sunflower plants effectively is overcome.

DETAILED DESCRIPTION OF THE INVENTION

Figure 8:
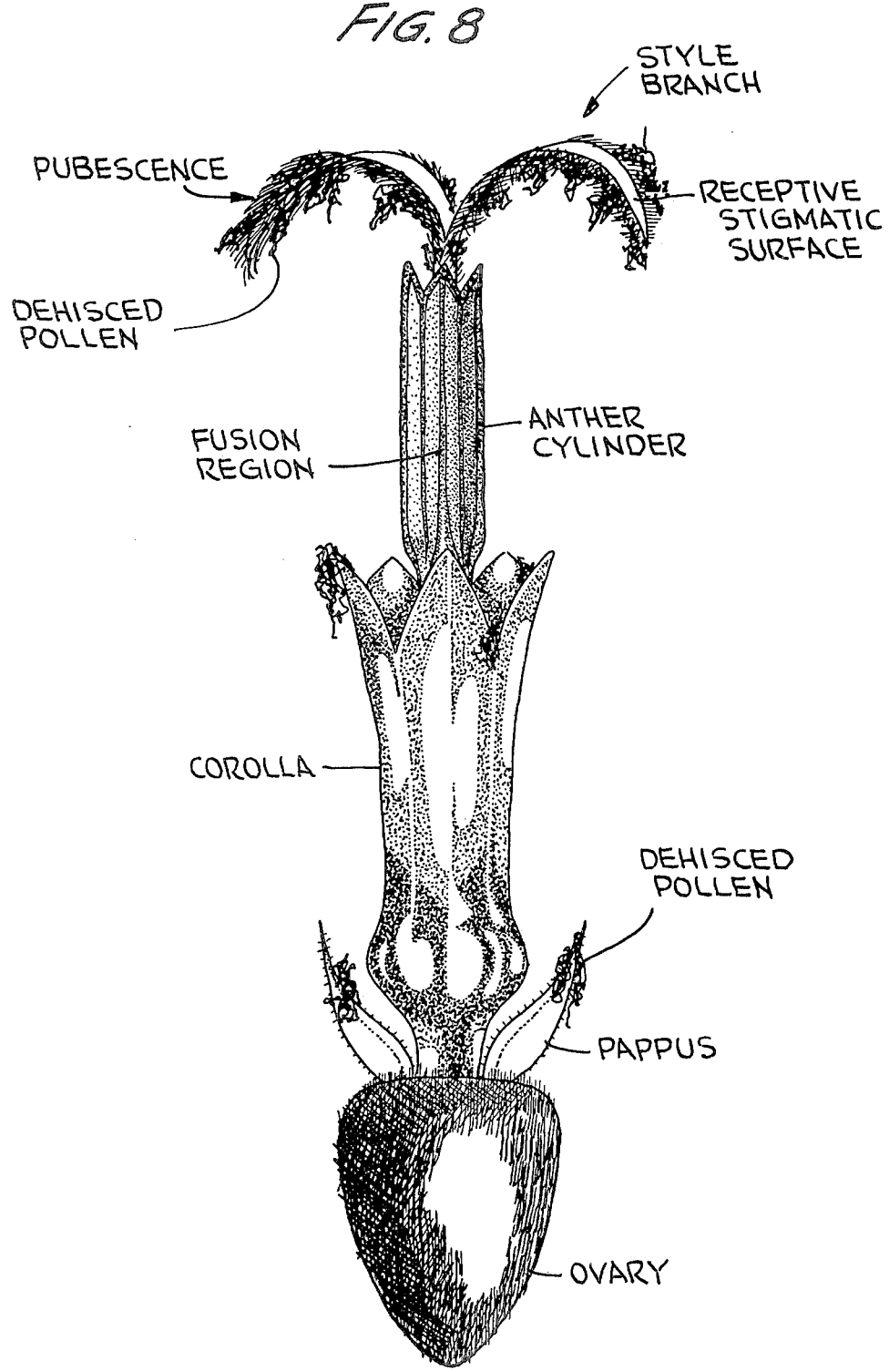
FIG. 8 is an enlarged schematic presentation of a typical sunflower floret at approximately 2½ hours following dawn. The style branches now are fully separated. Although most remaining pollen adheres to the pubescent underside of the style branches, it is excluded from the stigmatic surfaces. At this point the stigmatic surfaces are highly receptive to all pollen that can be exposed to it. Pollen is dropping all around the floret except on the stigmatic surfaces.
Figure 9:
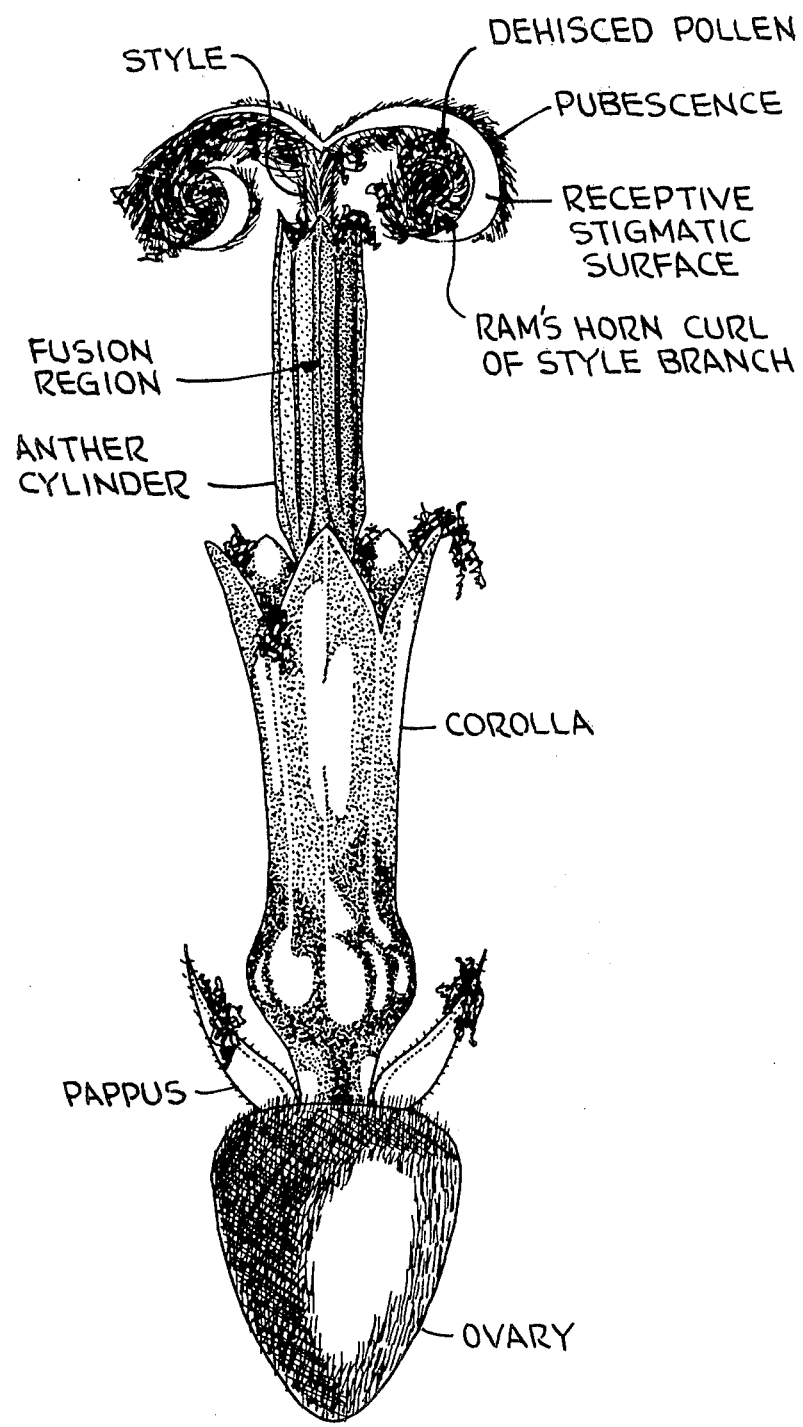
FIG. 9 is an enlarged schematic presentation of a typical sunflower floret the following day (i.e. approximately 24 hours following FIG. 2). The style branches now have curled into a "ram's horn" curl thus exposing a portion of the stigmatic surfaces to residual pollen which has adhered to the pubescent under surfaces of the style branches. In the event that out-crosses failed, the plant now has an opportunity to a limited degree to self-pollinate assuming that it is sufficiently self-compatible (i.e. self-fruitful) to do so. In a hot dry environment the pollen will already likely be dead at this point in time. Under more moderate climatic conditions some of the pollen will still be alive so that self-pollination can be accomplished within some florets. The "ram's horn" curl is not present in all sunflower florets; however, most domesticated and non-domesticated sunflower plants exhibit this feature in varying degrees.

As illustrated in FIGS. 1 through 10, typical sunflower florets have been found to possess heavy collenchyma cells between anthers which form a strong and impervious fused anther cylinder which opens only at the end to dispell pollen. Accordingly, in prior art processes for the production of sunflower seeds there inherently has been a mechanical impediment to achieving self-fertilization even if the physiological or sporophytic self-incompatability found in nature is effectively overcome.

During early 1974 I obtained from the Canadian Federal Station at Morden, Manitoba, Canada, an experimental sunflower seed sample designated to be a composite cross. Such seed sample was highly heterogeneous and is believed to have been formed by the crossing of many different and unspecified sunflower cultivars. Accordingly, it was capable of yielding a highly variable population of sunflower plants. This seed sample was planted by me or those acting under my direct supervision in a test growing area at Fresno, Calif. for study during the Summer of 1974. As buds were formed upon the resulting sunflower plants, transparent bags were placed over the same to insure that pollen from other plants would not reach the stigmatic surfaces. The volume of resulting seed formation was observed under these conditions and selection was made on this basis (i.e. on the basis of self-compatability as evidenced by the level of seed set). The seed resulting from this selection was planted by me or those acting under my direct supervision at the same test growing area at Fresno, Calif. during the Summer of 1975. As buds were formed upon the resulting sunflower plants, transparent bags were again placed over the same to insure that pollen from other plants would not reach the stigmatic surfaces. Selection was again made on the basis of the volume of seed formation. To the best of my knowledge all sunflower blossoms formed during the heretofore described plant engineering research involving progeny of the Morden composite cross during the Summers of 1974 and 1975 possessed the typical sunflower floret characteristics illustrated in FIGS. 1 through 10.

During the Winter of 1975-1976 the seeds resulting from the prior selections were planted by me or those acting under my direct supervision at a test growing area located on the Molokai Island of Hawaii. As the buds were formed upon the resulting sunflower plants, transparent bags were again placed over the same to insure that pollen from other plants would not reach the stigmatic surfaces. In culture Row No. 222 of this growing area it was observed by me that an atypical mutant character concerning floret appearance was manifest for the first time in addition to sporophytic or physiological self-compatibility. Such mutant character had never heretofore been described in the literature to the best of my knowledge and its true significance was not immediately apparent. This was subsequently confirmed by me to be the mutant character illustrated in FIGS. 11 through 13.

Even upon observing such atypical floret appearance it was not obviously apparent that such plants would be of any utility whatsoever, and it particularly was not obviously apparent that sunflower plants with such appearance could be used as a key element in an improved process (as described herein) for the production of sunflower seeds in increased yields. Reasons for such conclusions include the following:

(1) Little is known or has been published concerning the detailed anatomical characteristics of sunflower blossoms (See Chapter II of the Heiser treatise which tends primarily to be a description of the physical appearance of a sunflower blossom when fully mature).

(2) Little is known of the developmental morphology or etiology of the anther cylinder and style in the sunflower, and there is no known prior description as set forth herein concerning FIGS. 1 to 10. This was developed as a result of my research.

(3) When sporophytic sunflower rejection mechanisms were reported by E. C. Habura in "Parasterilitaet bei Sonnenplumen", Ztcher. f. Pflanzenzuchung, 37:280–298 (1957) it was assumed the physiological type of incompatability was the one used by the *Helianthus* genus. The sporophytic rejection is so strong in the naturally-occurring relatives of the domesticated sunflower that self-pollination is almost unknown even when pollen is carefully placed upon the receptive stigmatic surface. This is also true, though not to the same degree, for synthetic sunflower cultivars developed over the past seventy-five years.

(4) Other researchers largely had directed their efforts toward attempting to enhance sunflower cross-pollination (i.e. away from self-pollination) and the production of hybrids so that hybrid vigor would be exhibited in the hope that this would lead to a larger crop of sunflower seeds.

(5) The appearance of the disk in the bloom is ragged and would be rated very poor.

(6) One would erroneously assume that the anthers are abnormal and poorly developed upon observing the abnormal sunflower disk.

(7) One would erroneously assume that the pollen yield is very poor upon observing the abnormal sunflower disk.

(8) Due to early pollination the style does not extend very far beyond the corolla, thus giving the appearance of a poorly developed pistillate flower, and some florets may even be considered sterile as the pistil collapses after pollination.

Even if some of these factors were not accepted by a given researcher of ordinary skill in the art at the time the invention was made (which is unlikely) other factors would be expected to have led to the same conclusions expressed above. In fact, any one of these factors would tend to have lead a researcher interested in improving the sunflower crop to discard the newly developed mutant. It was only through acute observation and careful dissection of the florets that the nature of the mutant became known.

Figure 13:
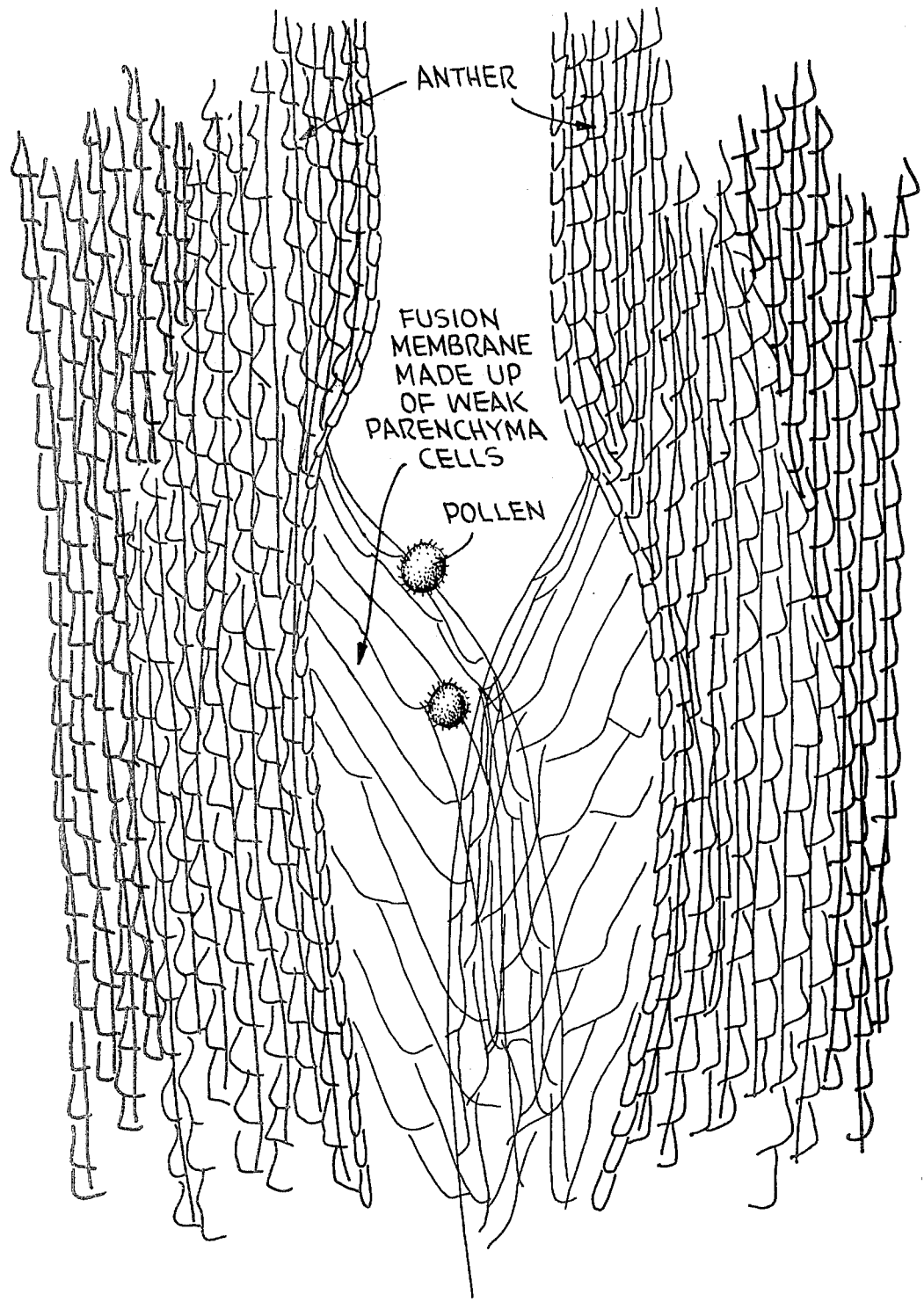
FIG. 13 is a much enlarged schematic presentation of a portion of a sunflower floret which illustrates the fused region present between adjoining anthers of the atypical sunflower floret developed by me prior to rupture. The fusion membrane between anthers is composed of weak parenchyma cells that are easily ruptured. Pollen grains of approximately 40 microns in diameter also are illustrated. Compare FIG. 13 to the fused region of a typical sunflower floret illustrated in FIG. 10.

During the Winter of 1975–1976 crosses were attempted at Molokai Island by me or those acting under my direct supervision between this newly developed mutant from Row No. 222 and pollen from other cultivars, as well as pollen from other plants exhibiting the same character in Row No. 222. These and subsequent studies have confirmed this atypical sunflower plant to be as illustrated in FIGS. 11 through 13. Such plants were found to not only have overcome the usual sporophytic or physiological selfincompatability, but the typical mechanical incompatibility as well. The pollen yield was, in fact, ample, the anthers were fully developed, and the pistillate flower was fully developed as well.

Figure 10:
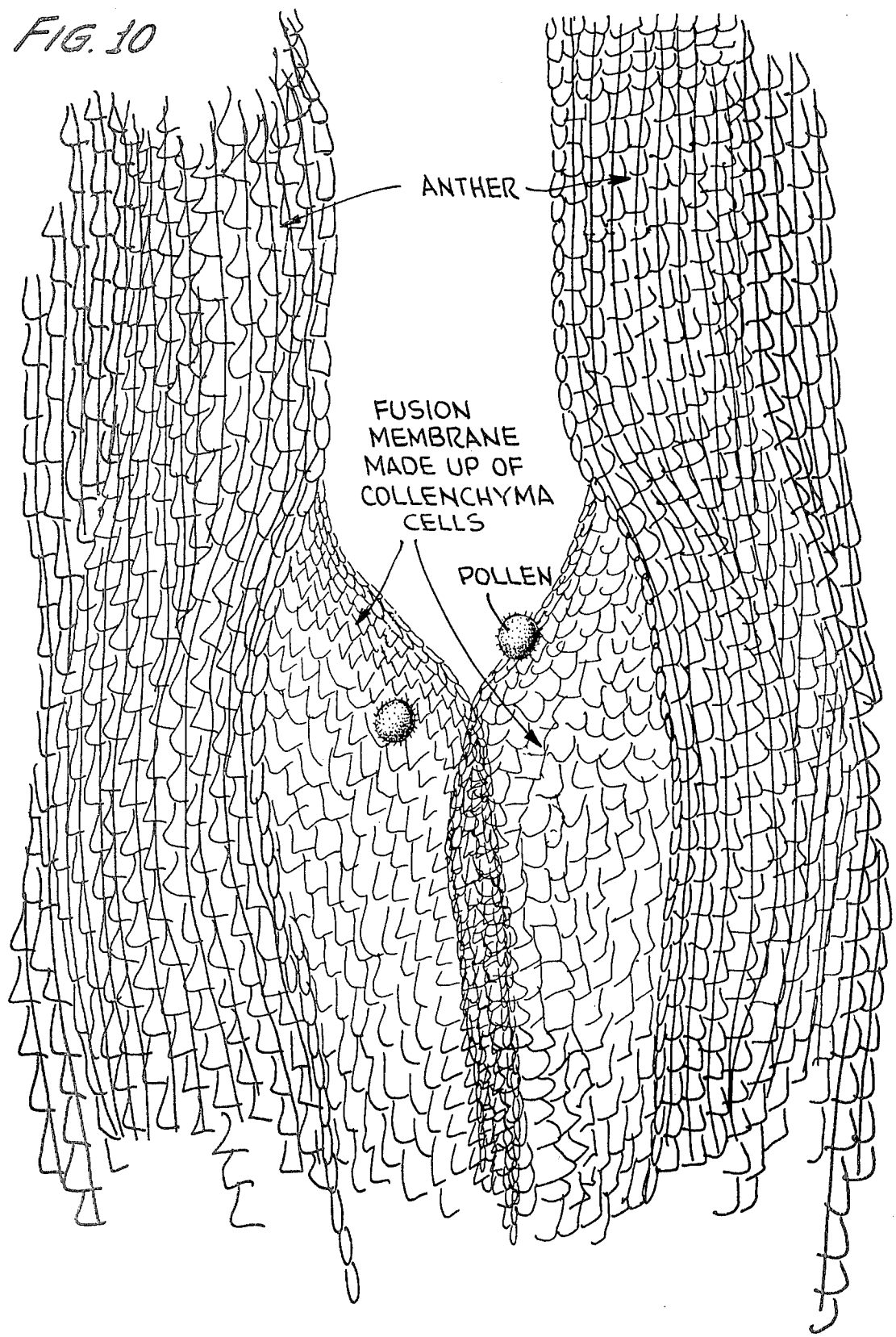
FIG. 10 is a much enlarged schematic presentation of a portion of a typical sunflower floret which illustrates the fused region present between adjacent anthers of the normal fused anther cylinder. The fusion membrane between anthers is composed of heavy collenchyma cells that are resistant to tearing. Pollen grains of approximately 40 microns in diameter also are illustrated.

The key area of abnormality in such plants was found to reside in the nature of cells which serve to bind adjacent anthers to form the anther cylinder. As illustrated in FIG. 10, in the normal sunflower plant the anthers are fused together by heavy collenchyma cells which are tough and resistant to rupturing and tearing following pollen dehiscence (i.e. they remain as an intact fused area between anthers). However, in the sunflower plants developed in Row No. 222 the anthers were fused by weak parenchyma cells as illustrated in FIG. 13. The terms "collenchyma" are "parenchyma" as used herein are consistent with the usage described in Page 4, of "Anatomy of Seed Plants", 2nd Edition, John Wiley & Sons (1977) by K. Esau which is herein incorporated by reference. Such weakly fused anther cylinder readily ruptures between adjacent anthers when the piston-like action of the style begins to force the pollen out of the cylinder immediately following pollen dehiscence. When the cylinder ruptures, the style next branches apart, thereby exposing the receptive stigmatic surfaces to the newly dehisced pollen. This action provides the opportunity for self-pollination much earlier than when the normal sunflower pollination procedure is followed. The consequences of this abnormality is a higher percentage of fertilized ovules (i.e. increased seed formation) even in the absence of pollen-carrying insects.

It has been found that the existence of sunflower plants having parenchyma cells between floret anthers which allow the anthers to become substantially non-fused following pollen dehiscence is controlled by a dominant-recessive gene mechanism heretofore unknown in sunflower plants. The existence of such weak parenchyma cells between the anthers of the anther cylinder is believed to be the result of the expression of a pair of homozygous recessive genes which have been designated "f genes". Such conclusion was confirmed, inter alia, by initial experiments wherein a sunflower plant with collenchyma cells between anthers was crossed to a plant from Row No. 222 exhibiting parenchyma cells between anthers. More specifically, at Molokai Island during the Summer of 1976 the plant with normal cells between anthers was hand emasculated and then pollinated with pollen from the plant having the abnormal non-fused anther character. The resulting $F_1$ hybrid seed was planted by me or those acting under my direct supervision at Molokai Island during January, 1977. Each of the resulting $F_1$ plants was found to have the normal collenchyma cells between anthers of the anther cylinder. Each of these $F_1$ plants was then self-pollinated to form a segregating generation (i.e. an $F_2$ generation ) and then backcrossed to another plant having the abnormal non-fused anther character. The first segregating generation and the first backcross generation were grown at Freson, Calif. during the Summer of 1977, and data was collected with respect to the frequency of the normal and abnormal cell characters between anthers within each culture. Four out of five of these cultures tested fit the postulated 3:1 normal/abnormal ratio in the segregating generation (i.e. the $F_2$ generation) thereby establishing the single dominant-recessive gene mechanism for this character.

On the same date the present application is being filed in the U.S. Patent and Trademark Office I am causing to be deposited in the National Seed Storage Laboratory located at Fort Collins, Colo., sunflower seed samples possessing the requisite homozygous f genes to carry out various embodiments of the process of the present invention. My sample No. 405 A (Laboratory Accession No. HA-82, Serial No. 100,331) is a cultivar consisting of a homogeneous assemblage of seeds which upon growth yield cytoplasmic male sterile sunflower plants which possess the homozygous f genes. My Sample No. 405B (Laboratory Accession No. HA-83, Serial No. 100332) is a cultivar consisting of a homogeneous assemblage of seeds which upon growth yield maintainer sunflower plants for the cytoplasmic male sterile characteristic of the above sample and additionally possess the homozygous f genes.

The homozygous f gene character can be transferred from a given source into other sunflower inbred lines and cultivars by plant breeding techniques such as the backcross method, and the pedigree method (i.e. the progeny row method) taking due consideration of the dominant-recessive mechanism shown to be operative, and the combining ability of the plants involved. Such techniques are known to those skilled in plant breeding and can be conventionally applied. Once one is in possession of a new sunflower plant possessing otherwise desirable characteristics (e.g. drought resistance, disease resistance, etc.) in which the homozygous f genes are also manifest, it can thereafter be developed into a homogeneous stable line or strain through such breeding techniques followed by selection.

For instance, homozygous f genes can be transferred into a previously existing sunflower inbred line by crossing a normal inbred patent (which has been hand emasculated) with pollen from a plant which manifests the homozygous f genes, self-pollinating the resulting $F_1$ generation, selecting plants which manifest the homozygous f genes from the resulting $F_2$ generation, backcrossing such plants with the normal inbred parent, self-pollinating the resulting $F_1$ generation, selecting plants which manifest the homozygous f genes, backcrossing such plants with the normal inbred parent, self-pollinating the resulting $F_1$ generation, selecting plants which manifest the homozygous f genes, backcrossing such plants with the normal inbred parent, self-pollinating the resulting $F_1$ generation, and selecting for the inbred parent type which manifests the homozygous f genes. The same procedure can be utilized to transfer the homozygous f genes into the parents of genetic sterile sunflower plants.

A new inbred line which manifests the f gene can be developed by crossing a parent processing desirable characteristics (which has been hand emasculated) with a parent possessing the homozygous f genes, self-pollinating the resulting $F_1$ generation to form a large $F_2$ population, selecting those plants which manifest the homozygous f genes as well as other desirable characteristics, self-pollinating the plants resulting from such selection whereby all progeny manifest the homozygous f genes, selecting again for those plants having the most desirable characteristics, self-pollinating the plants having the most desirable characteristics, and continuing until an acceptable new inbred sunflower line is obtained.

Cytoplasmic male sterile cultivars can be developed which additionally manifest the homozygous f gene characteristic. As will be apparent to those skilled in the art, in this instance three different cultures can be used as follows: (1) a conventional cytoplasmic male sterile line which does not manifest the homozygous f genes, (2) a conventional maintainer line which when crossed with a cytoplasmic male sterile line is capable of forming seed on the male sterile plants which is capable of forming cytoplasmic male sterile plants to the substantial exclusion of male fertile plants, and (3) a plant source which manifests the homozygous f genes. Initially the maintainer line is hand emasculated and pollinated with pollen from the homozygous f gene source to form an $F_1$ generation which possesses normal collenchyma cells. The $F_1$ generation is self-pollinated. The $F_2$ generation segregates 3:1 (F:f). The plants exhibiting homozygous f genes are backcrossed to the recurrent parent and crossed to the sterile simultaneously. The procedure is continued until the resulting offspring which possess the f genes in homozygous condition have a minimum of four doses of the recurrent parent.

The process of the present invention offers the sunflower grower (i.e. the farmer) as well as others interested in the multiplication of sunflower lines and cultivars for sale to the grower the ability to produce sunflower seeds in increased yields within a given growing area. In one embodiment of the invention a plurality of seeds capable of forming sunflower plants which are physiologically self-compatible and possess homozygous f genes are planted in a growing area. Such plurality of seeds which are planted may be capable of forming a male fertile inbred line, a male fertile cultivar, or optionally be capable of forming an $F_1$ hybrid (e.g. be the result of the crossing of a cytoplasmic male sterile sunflower plant and a restorer sunflower plant with respect to the sterility). Such planting is carried out in the substantial absence of seeds capable of forming sunflower plants which are physiologically self-incompatible and/or which lack the homozygous f genes. Upon germination sunflower plants are produced and seeds are formed on such sunflower plants in increased yields as a result of self-pollination made possible by the parenchyma cells between floret anthers which allow the anthers to become substantially non-fused immediately following pollen dehiscence. The resulting sunflower seeds next are harvested.

In another embodiment of the present invention sunflower seeds capable of forming $F_1$ hybrid sunflower plants which in turn yield sunflower seeds in increased yields are formed. A first substantially uniform population of male sterile sunflower plants which possess homozygous f genes are grown in pollinating proximity to a second substantially uniform population of male fertile sunflower plants which also possess the homozygous f genes. The plants of the first population are pollinated with pollen derived from the second population by the aid of pollen-carrying insects, and the sunflower seeds formed as a result of such cross-pollination are selectively recovered from the plants of the first population.

The sterility exhibited by the plants of the first population can be of varied origin. For instance, it can be cytoplasmic, genetic, or induced by the application of gameticide (e.g. gibberellic acid) in accordance with known techniques. In a particularly preferred embodiment (which is highly suitable for commercial seed production) the sunflower plants of the first population are cytoplasmic male sterile, and the male fertile plants of the second population are restorer plants with respect to the male sterility. In such instance $F_1$ hybrid seeds are formed on the plants of the first population which upon growth yield sunflower plants which are uniformly physiologically self-compatible and also possess the homozygous f genes. On the contrary, should the plants of the first population be genetic male sterile it will be essential for the grower of the seeds planted to form the first population to first rogue out those resulting sunflower plants in which such sterility is not exhibited so that only sterile sunflower plants remain to be pollinated. In such instance $F_1$ hybrid seeds are formed on that portion of the original population which exhibited male sterility.

Conventional techniques can be utilized when planting the first and second populations heretofore described. For instance, the plants of each population can be planted in adjacent alternating strips. An effective alternating growing pattern consists of approximately eight rows of the plants of the first population per one row of the plants of the second population.

Pollen-carrying insects (i.e. insect vectors) are utilized to affect the pollen transfer required to accomplish cross-pollination, with the pollen being transferred from the second to the first population of sunflower plants. Such pollen-carrying insects preferably are bees (e.g. honey bees).

The sunflower seeds capable of forming $F_1$ hybrid sunflower plants which are harvested from the plants of the first population can be planted by a sunflower grower to form sunflower plants capable of forming sunflower seeds in increased yields because of the presence of the homozygous f genes and the accompanying parenchyma cells between anthers.

The sunflower seeds formed on the plants of the second population as a result of self-pollination additionally can selectively be harvested. Such seed will be inherently incapable of forming $F_1$ hybrid sunflower plants. It can, however, be used for other purposes including the perpetuation and multiplication of the inbred line, or as a source for food and/or oil.

Whenever an embodiment of the present process is carried out wherein the desired pollination is one of self-pollination which is expedited by the presence of the parenchyma cells, it is not essential that one rely upon pollen-carrying insects to aid in such pollination. Such self-pollination has been found to occur on an efficient basis even in the absence of pollen-carrying insects. Accordingly, the grower may choose to treat the resulting sunflower blossoms with an insecticide in order to control the sunflower head moth (i.e. *Homeosoma ellectelum*) without substantially impairing the increased seed yield as a result of the concomitant destruction of needed pollen-carrying insects.

Process embodiments of the present invention make possible the harvest of a *Helianthus annuus* seed product consisting of a substantially homogeneous assemblage of seeds which upon growth yield sunflower plants which are physiologically self-compatible and possess homozygous f genes, wherein the f genes facilitate the formation of parenchyma cells between floret anthers which allow the anthers to become substantially non-fused prior to pollen dehiscense thereby making possible a greater degree of self-pollination with concomitant increased seed formation. Such seeds additionally may be capable of forming $F_1$ hybrid sunflower plants. Such substantially homogeneous seed product can be marketed in bags or other containers.

When sunflower plants possessing the homozygous f genes and the parenchyma cells between anthers are grown, increased seed yields are made possible even under adverse growing conditions. The relative amount of increased yield commonly will vary with the environmental conditions encountered by the sunflower plants. Such relative amount of increased yield tends to be the greatest under adverse growing conditions such as when the daytime temperature is high (e.g. 100° F.) and the relative humidity low (e.g. below 20 percent). It is under such conditions that the pollen longevity is the lowest when one is attempting to pollinate typical sunflower florets of existing commercial sunflower cultivars possessing collenchyma cells between anthers. Under these adverse conditions even the "ram's horn" curl of the style branches (See FIG. 9) cannot be depended upon to accomplish much self-fertilization. However, in accordance with the process of the present invention good pollination (e.g. a 50 percent increase) can be accomplished under these circumstances. In those instances when more moderate growing conditions are encountered the relative amount of increased yield is not so dramatic when compared to existing commercial sunflower cultivars; however, an increased yield (e.g. a 12 percent increase) is made possible since substantial numbers of typical sunflower florets possessing collenchyma cells between anthers commonly escape pollination when such sunflower plants are grown in large numbers on a commercial scale. The improved sunflower growing process of the present invention accordingly offers the grower a greater assurance of ample seed production regardless of the growing conditions which ultimately are encountered.

Although the invention has been described with preferred embodiments, it is to be understood that variations and modifications may be resorted to as will be apparent to those skilled in the art. Such variations and modifications are to be considered within the purview and scope of the claims appended hereto.

I claim:

1. A process for the production of sunflower seeds in increased yields comprising:
    (a) planting in a growing area a plurality of seeds capable of forming *Helianthus annuus* sunflower plants which are physiologically self-compatible and possess homozygous f genes, said planting being carried out in the substantial absence of seeds capable of forming *Helianthus annuus* sunflower plants which are physiologically self-incompatible and/or lack homozygous f genes, whereby said seeds germinate to form sunflower plants, and seeds are formed on said sunflower plants as a result of self-pollination, said f genes having the ability to facilitate the formation of parenchyma cells between floret anthers which allow the anthers to become substantially non-fused following pollen dehiscence thereby making possible a greater degree of self-pollination with concomitant increased seed formation, and (b) harvesting said resulting seeds formed on said sunflower plants.

2. A process according to claim 1 wherein said plurality of seeds capable of forming *Helianthus annuus* sunflower plants which are planted are capable of forming $F_1$ hybrid sunflower plants and are the result of the crossing of a cytoplasmic male sterile sunflower plant and a restorer sunflower plant with respect to said sterility.

3. A process according to claim 1 wherein said plurality of seeds capable of forming *Helianthus annuus* sunflower plants which are planted are a male fertile inbred line.

4. A process according to claim 1 wherein said resulting sunflower plants additionally are treated with an insecticide to control sunflower head moths without substantially impairing said increased yields of sunflower seeds produced thereon as a result of the concomitant destruction of pollen-carrying insects.

5. A process for the production of sunflower seeds capable of forming $F_1$ hybrid sunflower plants which yield sunflower seeds in increased yields comprising:
 (a) growing a first substantially uniform population of male sterile *Helianthus annuus* sunflower plants which possess homozygous f genes, said f genes having the ability to facilitate the formation of parenchyma cells between floret anthers which allow the anthers in the resultant hybrid to become substantially non-fused following pollen dehiscence,
 (b) growing a second substantially uniform population of male fertile *Helianthus annuus* sunflower plants which possess said homozygous f genes in pollinating proximity to said first substantially uniform population,
 (c) cross-pollinating said plants of said first substantially uniform population with pollen derived from said plants of said second population with the aid of pollen-carrying insects, and
 (d) selectively recovering sunflower seeds which are formed upon said plants of said first population.

6. A process for the production of sunflower seeds capable of forming $F_1$ hybrid sunflower plants which yield sunflower seeds in increased yields according to claim 5 wherein said male sterile plants of said first substantially uniform population are cytoplasmic male sterile, and said male fertile plants of said second substantially uniform population are restorer plants with respect to said male sterility.

7. A process for the production of sunflower seeds capable of forming $F_1$ hybrid sunflower plants which yield sunflower seeds in increased yields according to claim 5 wherein said male sterile plants of said first substantially uniform population are genetic male sterile.

8. A process for the production of sunflower seeds capable of forming $F_1$ hybrid sunflower plants which yields sunflower seeds in increased yields according to claim 5 wherein said plants of said first and second second populations are grown in alternating strips.

9. A process for the production of sunflower seeds capable of forming $F_1$ hybrid sunflower plants which yield sunflower seeds in increased yields according to claim 5 which includes the additional step of selectively recovering sunflower seeds which are formed upon said second population.

10. A process for the production of sunflower seeds capable of forming $F_1$ hybrid sunflower plants in increased yields according to claim 5 wherein said pollen-carrying insects are bees.

11. A process for the production of sunflower seeds capable of forming $F_1$ hybrid sunflower plants which yield sunflower seeds in increased yields according to claim 5 which includes the additional step of (e) planting at least a portion of the sunflower seeds recovered from said plants of said first population, whereby said seeds germinate to form $F_1$ hybrid sunflower plants, and seeds are formed in increased yields on said sunflower plants as a result of self-pollination.

12. A process for the production of sunflower seeds capable of forming $F_1$ hybrid sunflower plants which yield sunflower seeds in increased yields according to claim 11 which includes the additional step of (f) treating said $F_1$ hybrid sunflower plants with an insecticide to control sunflower head moths without substantially impairing said increased yields of sunflower seeds produced thereon as a result of the concomitant destruction of pollen-carrying insects.

13. A process for the production of sunflower seeds in increased yields comprising:
 (a) growing a first substantially uniform population of cytoplasmic male sterile *Helianthus annuus* sunflower plants which possess homozygous f genes, said f genes having the ability to facilitate the formation of parenchyma cells between floret anthers which allow the anthers in the resultant hybrid to become substantially non-fused following pollen dehiscence,
 (b) growing a second substantially uniform population of restorer male fertile *Helianthus annuus* sunflower plants with respect to said sterility which possess said homozygous f genes in pollinating proximity to said first substantially uniform population,
 (c) cross-pollinating said plants of said first substantially uniform population with pollen derived from said plants of said second population with the aid of pollen-carrying insects,
 (d) selectively recovering $F_1$ hybrid sunflower seeds which are formed upon said plants of said first population, said seeds upon growth yielding sunflower plants which are physiologically self-compatible and which possess said homozygous f genes,
 (e) selectively recovering sunflower seeds which are formed upon said second population,
 (f) planting at least a portion of said $F_1$ hybrid sunflower seeds, whereby said seeds germinate to form $F_1$ hybrid sunflower plants, and seeds are formed in increased yields on said sunflower plants as a result of self-pollination, and
 (g) treating said $F_1$ hybrid sunflower plants with an insecticide to control sunflower head moths without substantially impairing said increased yield of sunflower seeds produced thereon as a result of the concomitant destruction of pollen-carrying insects.

14. A process for the production of sunflower seeds in increased yields according to claim 13 wherein said plants of said first and second populations are grown in alternating strips.

15. A process for the production of sunflower seeds in increased yields according to claim 13 wherein said pollen-carrying insects are bees.

16. A *Helianthus annuus* seed product consisting of a substantially homogeneous assemblage of seeds which upon growth yield sunflower plants which are physiologically self-compatible and possess homozygous f genes, wherein said f genes facilitate the formation of parenchyma cells between floret anthers which allow the anthers to become substantially non-fused prior to pollen dehiscense thereby making possible a greater degree of self-pollination with concomitant increased seed formation.

17. A *Helianthus annuus* seed product according to claim 16 wherein said seeds of said substantially homogeneous assemblage upon growth are additionally capable of forming $F_1$ hybrid sunflower plants.

* * * * *